United States Patent
Scaiano et al.

(10) Patent No.: US 10,423,803 B2
(45) Date of Patent: *Sep. 24, 2019

(54) SMART SUPPRESSION USING RE-IDENTIFICATION RISK MEASUREMENT

(71) Applicant: PRIVACY ANALYTICS INC., Ottawa (CA)

(72) Inventors: Martin Scaiano, Ottawa (CA); Andrew Baker, Ottawa (CA); Stephen Korte, Ottawa (CA)

(73) Assignee: PRIVACY ANALYTICS INC., Ottawa, On (CA)

( * ) Notice: Subject to any disclaimer, the term of this patent is extended or adjusted under 35 U.S.C. 154(b) by 156 days.

This patent is subject to a terminal disclaimer.

(21) Appl. No.: 15/389,559

(22) Filed: Dec. 23, 2016

(65) Prior Publication Data

US 2017/0103232 A1 Apr. 13, 2017

Related U.S. Application Data

(63) Continuation-in-part of application No. 15/320,240, filed as application No. PCT/CA2016/050381 on Apr. 1, 2016.

(Continued)

(51) Int. Cl.
G06F 21/62 (2013.01)
G16H 10/60 (2018.01)

(52) U.S. Cl.
CPC ......... *G06F 21/6254* (2013.01); *G16H 10/60* (2018.01); *Y02A 90/26* (2018.01)

(58) Field of Classification Search
CPC ...... G06F 21/6254; G16H 10/60; Y02A 90/26

(Continued)

(56) References Cited

U.S. PATENT DOCUMENTS 9,442,980 B1 * 9/2016 Trepetin ............ G06F 17/30477
2002/0169793 A1 11/2002 Sweeney
(Continued)

OTHER PUBLICATIONS

Gkoulalas-Divanis, et al., "Publishing data from electronic health records while preserving privacy: A survey of algorithms," Jun. 14, 2014, Elsevier, Journal of Biomedical Informatics 50, pp. 4-19 (Year: 2014).*

(Continued)

*Primary Examiner* — Harunur Rashid
*Assistant Examiner* — Sakinah White Taylor
(74) *Attorney, Agent, or Firm* — John Maldjian; Maldjian Law Group LLC

(57) ABSTRACT

System and method to produce an anonymized cohort, members of the cohort having less than a predetermined risk of re-identification. The method includes receiving a data query of requested traits to request in an anonymized cohort, querying a data source to find records that possess at least some of the traits, forming a dataset from at least some of the records, and calculating an anonymity histogram of the dataset. For each patient record within the dataset, the method anonymizes the dataset by calculating using a threshold selector whether a predetermined patient profile within the dataset should be perturbed, calculating using a value selector whether a value within the indicated patient profile should be perturbed, and suppressing an indicated value within the indicated patient profile. The anonymized dataset then is returned.

16 Claims, 4 Drawing Sheets

Related U.S. Application Data

(60) Provisional application No. 62/193,024, filed on Jul. 15, 2015.

(58) Field of Classification Search
USPC .......................................................... 726/26
See application file for complete search history.

(56) References Cited

U.S. PATENT DOCUMENTS

| | | | |
|---|---|---|---|
| 2003/0061510 A1* | 3/2003 | Hartmann ............... | H04L 63/04 726/23 |
| 2009/0030818 A1* | 1/2009 | Braun .................... | G06Q 40/06 705/30 |
| 2010/0077006 A1* | 3/2010 | El Emam ............ | G06F 21/6254 707/785 |
| 2010/0100577 A1* | 4/2010 | Middleton .......... | H01J 49/0036 708/308 |
| 2010/0114840 A1 | 5/2010 | Srivastava | |
| 2010/0332537 A1 | 12/2010 | El Emam et al. | |
| 2011/0178943 A1 | 7/2011 | Motahari | |
| 2011/0258206 A1 | 10/2011 | El Emam | |
| 2013/0208966 A1* | 8/2013 | Zhao ..................... | G06F 9/5072 382/131 |
| 2014/0019194 A1 | 1/2014 | Anne | |
| 2014/0081652 A1 | 3/2014 | Klindworth | |
| 2014/0189858 A1* | 7/2014 | Chen ................. | G06F 17/30289 726/22 |
| 2014/0304244 A1 | 10/2014 | Toyoda | |
| 2015/0007249 A1* | 1/2015 | Bezzi .................. | G06F 21/6254 726/1 |
| 2015/0033356 A1 | 1/2015 | Takenouchi | |
| 2015/0067602 A1* | 3/2015 | Bernstein ............. | G06F 3/0488 715/823 |
| 2015/0128285 A1 | 5/2015 | Lafever et al. | |
| 2015/0169895 A1 | 6/2015 | Gkoulalas-Divanis et al. | |
| 2015/0356591 A1 | 12/2015 | Fano | |
| 2016/0034703 A1 | 2/2016 | Dubov | |
| 2016/0203172 A1 | 7/2016 | Attaluri | |
| 2016/0248799 A1 | 8/2016 | Ng | |
| 2017/0243028 A1 | 8/2017 | LaFever | |
| 2018/0114037 A1 | 4/2018 | Scaiano | |

OTHER PUBLICATIONS

Tamersoy, et al. "Anonynnization of Longitudinal Electrical Medical Records," May 3, 2012, IEEE Transactions on Information Technology in Biomedicine, 16, pp. 413-423 (Year: 2012).*

Diaz, C. et al., "Information Theory and Anonymity", Proceedings of the 23rd Symposium on Information Theory in the Benelux, Louvain la Neuve, Belgium, (8 pages total) (May 29, 2002).

Bezzi, M., "An Entropy based method for measuring anonymity", , Proceedings of the IEEE Third International Conference on Security and Privacy in Communications Networks and the Workshops, SecureComm 2007, Nice, France, (5 pages, total) (Sep. 17, 2007).

Kounine, A et al., "Assessing Disclosure Risk in Anonymized Datasets", Proceedings of FloCon2008, Savannah, Georgia, USA, (4 pages total) (Jul. 1, 2008).

Serjantov, A et al., "Towards an Information Theoretic Metric for Anonymity", Proceedings of the Second International Workshop on Privacy Enhancing Technologies, PET 2002, San Francisco, CA, USA, (14 pages total) (Apr. 14, 2002).

Diaz, C. et al., "Towards measuring anonymity", Proceedings of the Second International Workshop on Privacy Enhancing Technologies, PET 2002, San Francisco, CA, USA, (15 pages total) (Apr. 14, 2002).

Trabelsi, S. et al., "Data Disclosure Risk Evaluation", Proceedings of the Fourth International Conference on Risks and Security of Internet and Systems (CRiSIS 2009), Toulouse, France, pp. 35-42 (8 pages total) (Oct. 19, 2009).

Toth, G. et al., "Measuring Anonymity Revisited", Proceedings of the Ninth Nordic Workshop on Secure IT, Espoo, Finland, (6 pages total) (Apr. 11, 2004).

Airoldi, E.M. et al., "An entropy approach to disclosure risk assessment: Lessons from real applications and simulated domains", Decision Support Systems, vol. 51, issue 1, pp. 10-20, (11 pages total) (Jan. 4, 2011).

International Search Report and Written Opinion dated Jun. 5, 2016 issued in connection with International Application No. PCT/CA2016/050381 (10 pages total).

* cited by examiner

300

400

SMART SUPPRESSION USING RE-IDENTIFICATION RISK MEASUREMENT

CROSS-REFERENCE TO RELATED APPLICATIONS

This application is a continuation-in-part of U.S. patent application Ser. No. 15/320,240, filed on Dec. 19, 2016, which claims benefit and priority to International Application No. PCT/CA2016/050381, filed Apr. 1, 2016, which claims priority to U.S. Provisional Application No. 62/193,024 filed Jul. 15, 2015, the entire contents of which are hereby incorporated by reference in its entirety.

BACKGROUND

Field

The present disclosure relates to risk assessment of datasets and in particular to reducing re-identification risk of a dataset.

Description of Related Art

Personal information is continuously captured in a multitude of electronic databases. Details about health, financial status and buying habits are stored in databases managed by public and private sector organizations. These databases contain information about millions of people, which can provide valuable research, epidemiologic and business insight. For example, examining a drugstore chain's prescriptions can indicate where a flu outbreak is occurring. To extract or maximize the value contained in these databases, data custodians often must provide outside organizations access to their data. In order to protect the privacy of the people whose data is being analyzed, a data custodian will "de-identify" or "anonymize" information before releasing it to a third-party. An important type of de-identification ensures that data cannot be traced to the person about whom it pertains, this protects against "identity disclosure".

When de-identifying records, removing just direct identifiers such as names and addresses is not sufficient to protect the privacy of the persons whose data is being released. The problem of de-identification involves personal details that are not obviously identifying. These personal details, known as quasi-identifiers, include the person's age, sex, postal code, profession, ethnic origin and income, financial transactions, medical procedures, and so forth. De-identification of data requires an assessment of the risk of re-identification.

Once the risk is determined, the risk may be reduced if necessary by use of suppression. Suppression is a risk mitigation technique that removes a field value from a dataset in order to lower risk. For example, suppose a re-identification risk of a database is measured. If the measured risk needs to be lowered, suppression may modify a field in the database by replacing actual data in the field with an analytic model of what the data in the field should be. However, if suppression is not done intelligently, the suppression may introduce problems in a returned dataset, and may take a relatively long time to produce a sufficiently anonymized dataset, i.e., a dataset that has been de-identified.

Previous techniques in the background art for suppression included picking values (e.g., picking a data field for all records in a database, or picking only specific records having predetermined value(s) in the data field), nulling out the picked values, re-measuring the re-identification risk, and then reiterating in a loop if the re-identification risk is still too high. In the background art, this iterative process was found to take excessive time to converge to a an acceptable solution, e.g., hours or days. In some cases, time to converge would be unknown because the process would be aborted by users as having exceeded their user tolerance.

Accordingly, systems and methods that enable improved risk assessment remains highly desirable.

BRIEF SUMMARY

Embodiments in accordance with the present disclosure provide a system and method to calculate a re-identification risk and predict a suppression that would be highly effective in reducing the re-identification risk. Embodiments may use local recoding, such that instead of removing the value, embodiments recode the value to another value. Local recoding is a variation of suppression.

An ability to make predictions enables embodiments to process a dataset in only a single pass, in contrast to methods of the background art that iteratively suppress by a trial amount, test for low risk, and repeat until adequate suppression is achieved. Before applying suppression, embodiments predict the risk after suppression if a certain amount would be applied. If the prediction is below the threshold then embodiments suppress by that certain amount. Embodiments are able to achieve acceptable levels of re-identification risk typically in only one pass.

Embodiments also provide a computational framework for future improvement that allows for substitution of different computational modules in order to provide additional suppression techniques. The smart suppression technique, which works within the computational framework, maintains better data quality and more efficiently lower risk of re-identification than previously naive or uninformed methods of the background art.

Embodiments perform local recoding, which is a more general version of suppression. Local recoding changes the value to something more meaningful and more accurate instead of completely deleting the value. For example, local recoding may replace a value with another value at a different generalization, instead of deleting or replacing the value with a NULL.

Embodiments in accordance with the present disclosure include a system and a method to produce an anonymized cohort, members of the cohort having less than a predetermined risk of re-identification. The method includes receiving a data query of requested traits to request in an anonymized cohort, querying a data source to find records that possess at least some of the traits, forming a dataset from at least some of the records, and calculating an anonymity histogram of the dataset. For each patient record within the dataset, the method anonymizes the dataset by calculating using a threshold selector whether a predetermined patient profile within the dataset should be perturbed, calculating using a value selector whether a value within the indicated patient profile should be perturbed, and suppressing an indicated value within the indicated patient profile. The anonymized dataset then is returned.

The preceding is a simplified summary of embodiments of the disclosure to provide an understanding of some aspects of the disclosure. This summary is neither an extensive nor exhaustive overview of the disclosure and its various embodiments. It is intended neither to identify key or critical elements of the disclosure nor to delineate the scope of the disclosure but to present selected concepts of the disclosure in a simplified form as an introduction to the more detailed description presented below. As will be appreciated, other embodiments of the disclosure are possible utilizing, alone or in combination, one or more of the features set forth above or described in detail below.

BRIEF DESCRIPTION OF THE DRAWINGS

The above and still further features and advantages of the present disclosure will become apparent upon consideration of the following detailed description of embodiments thereof, especially when taken in conjunction with the accompanying drawings wherein like reference numerals in the various figures are utilized to designate like components, and wherein.

Figure 1:
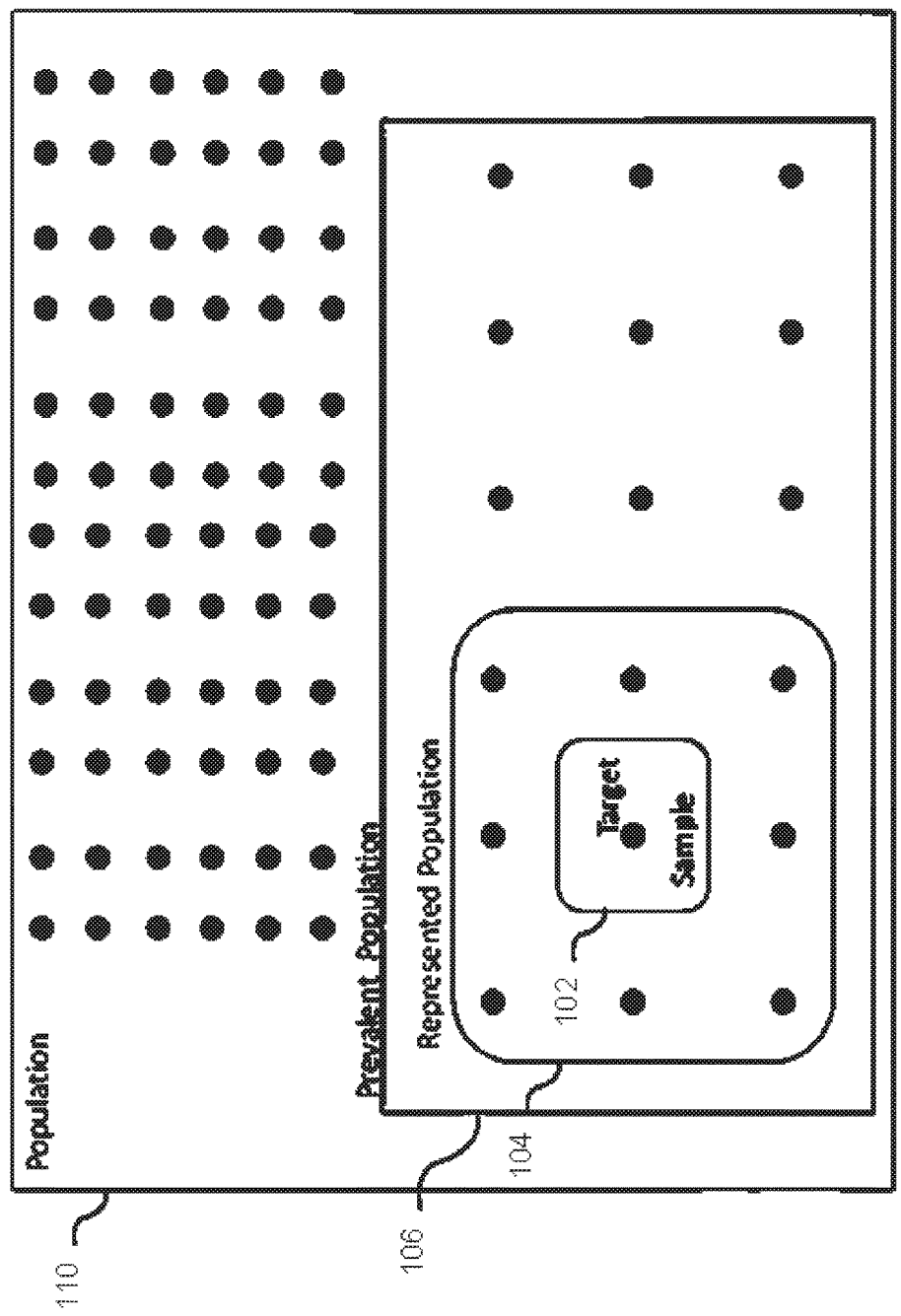
FIG. 1 shows a representation of a sample population in accordance with an embodiment of the present disclosure.

The headings used herein are for organizational purposes only and are not meant to be used to limit the scope of the description or the claims. As used throughout this application, the word "may" is used in a permissive sense (i.e., meaning having the potential to), rather than the mandatory sense (i.e., meaning must). Similarly, the words "include", "including", and "includes" mean including but not limited to. To facilitate understanding, like reference numerals have been used, where possible, to designate like elements common to the figures. Optional portions of the figures may be illustrated using dashed or dotted lines, unless the context of usage indicates otherwise.

DETAILED DESCRIPTION

The disclosure will be illustrated below in conjunction with an exemplary computing and storage system. Although well suited for use with, e.g., a system using a server(s), data sources and/or database(s), the disclosure is not limited to use with any particular type of computing, communication and storage system or configuration of system elements. Those skilled in the art will recognize that the disclosed techniques may be used in any computing, communication and storage application in which it is desirable to store protected data, such as medical data, financial data, educational records data, etc.

As used herein, the term "module" refers generally to a logical sequence or association of steps, processes or components. For example, a software module may include a set of associated routines or subroutines within a computer program. Alternatively, a module may comprise a substantially self-contained hardware device. A module may also include a logical set of processes irrespective of any software or hardware implementation.

A module that performs a function also may be referred to as being configured to perform the function, e.g., a data module that receives data also may be described as being configured to receive data. Configuration to perform a function may include, for example: providing and executing sets of computer code in a processor that performs the function; providing provisionable configuration parameters that control, limit, enable or disable capabilities of the module (e.g., setting a flag, setting permissions, setting threshold levels used at decision points, etc.); providing or removing a physical connection, such as a jumper to select an option, or to enable/disable an option; attaching a physical communication link; enabling a wireless communication link; providing electrical circuitry that is designed to perform the function without use of a processor, such as by use of discrete components and/or non-CPU integrated circuits; setting a value of an adjustable component (e.g., a tunable resistance or capacitance, etc.), energizing a circuit that performs the function (e.g., providing power to a transceiver circuit in order to receive data); providing the module in a physical size that inherently performs the function (e.g., an RF antenna whose gain and operating frequency range is determined or constrained by the physical size of the RF antenna, etc.), and so forth.

As used herein, the term "transmitter" may generally include any device, circuit, or apparatus capable of transmitting a signal. As used herein, the term "receiver" may generally include any device, circuit, or apparatus capable of receiving a signal. As used herein, the term "transceiver" may generally include any device, circuit, or apparatus capable of transmitting and receiving a signal. As used herein, the term "signal" may include one or more of an electrical signal, a radio signal, an optical signal, an acoustic signal, and so forth.

As will be appreciated by one skilled in the art, aspects of the present disclosure may be embodied as a system, method or computer program product. Accordingly, aspects of the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium excludes a computer readable signal medium such as a propagating signal. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: a portable computer diskette, a hard disk, a random access memory (RAM), a read-only memory (ROM), an erasable programmable read-only memory (EPROM or Flash memory), a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device. Program code embodied on a computer readable medium may be transmitted using any appropriate medium, including but not limited to wireless, wireline, optical fiber cable, RF, etc., or any suitable combination of the foregoing.

Embodiments are described below, by way of example only, with reference to FIGS. 1-4. The exemplary systems and methods of this disclosure will also be described in relation to software, modules, and associated hardware. However, to avoid unnecessarily obscuring the present disclosure, the following description omits well-known structures, components and devices that may be shown in block diagram form, are well known, or are otherwise summarized.

Certain sensitive personal information like patient health information is protected by law (e.g., Healthcare Information Portability and Accountability Act ("HIPAA," codified at 42 U.S.C. § 300gg and 29 U.S.C § 1181 et seq. and 42 USC 1320d et seq.) in the U.S.) and must be treated in a way that maintains patient privacy. Such information is termed protected health information (PHI). With respect to PHI, it is important to avoid disclosing the PHI of a specific patient, or to disclose PHI so specific that it discloses an identity of a specific patient. All stakeholders involved must accept their stewardship role for protecting the PHI data contained within. It is essential that systems that access the PHI do so in full compliance with HIPAA and any other applicable laws or regulations of the country concerned, and in a secure manner.

Patient information, including PHI, is sometimes needed for medical studies. For example, observational studies are an important category of study designs. For some kinds of investigative questions (e.g., related to plastic surgery), randomized controlled trials may not always be indicated or ethical to conduct. Instead, observational studies may be the next best method to address these types of questions. Well-designed observational studies may provide results similar to randomized controlled trials, challenging the belief that observational studies are second-rate. Cohort studies and case-control studies are two primary types of observational studies that aid in evaluating associations between diseases and exposures.

Three types of observational studies include cohort studies, case-control studies, and cross-sectional studies. Case-control and cohort studies offer specific advantages by measuring disease occurrence and its association with an exposure by offering a temporal dimension (i.e. prospective or retrospective study design). Cross-sectional studies, also known as prevalence studies, examine the data on disease and exposure at one particular time point. Because the temporal relationship between disease occurrence and exposure cannot be established, cross-sectional studies cannot assess the cause and effect relationship.

Cohort studies may be prospective or retrospective. Retrospective cohort studies are well-suited for timely and inexpensive study design. Retrospective cohort studies, also known as historical cohort studies, are carried out at the present time and look to the past to examine medical events or outcomes. A cohort of subjects, selected based on exposure status, is chosen at the present time, and outcome data (i.e. disease status, event status), which was measured in the past, are reconstructed for analysis. An advantage of the retrospective study design analysis is the immediate access to the data. The study design is comparatively less costly and shorter than prospective cohort studies. However, disadvantages of retrospective study design include limited control the investigator has over data collection. The existing data may be incomplete, inaccurate, or inconsistently measured between subjects, for example, by not being uniformly recorded for all subjects.

Some medical studies, such as retrospective cohort studies, may involve authorized access by medical researchers to anonymized PHI, i.e., to PHI that ideally is not identifiable with the original patient. However, in practice there is nonzero risk that the anonymized data may be re-identified back to the original patient, for example, if data selection criteria is excessively narrow, thus risking that a very small pool of patients meet the selection criteria.

Databases or datasets generated therefrom that contain personally identifiable information such as those used in medical and financial information can include a cross-sectional data (L1) in addition to longitudinal data (L2). Cross-sectional data includes a single record for each subject. A dataset is longitudinal if it contains multiple records related to each subject and the number of records may vary subject to subject. For example, part of a longitudinal dataset could contain specific patients and their medical results over a period of years. Each patient may have varying times and number of visits. In general a patient will only have a single gender, birthday, or ethnicity, which is consistent throughout his/her life. Longitudinal data are those values which exist an unknown number of times per patient. A patient may receive only a single diagnosis, or may be diagnosed with multiple different diseases. Some patients may not have any values for some longitudinal quasi-identifiers (QIs). An L2 group refers generically to a set of values drawn from one or more longitudinal tables which can be relationally linked together. A dataset may have more than one L2 group which cannot be inter-connected.

Such datasets are valuable in research and analytics, however the use of the datasets can provide an opportunity for attackers to determine personally identifiable information resulting in a data breach. In medical databases a patient can have multiple events based upon for example diagnoses, procedures, or medical visits defining L2 data.

Traditionally, if a risk of re-identification for a dataset is estimated to be too high (compared to a settable threshold), the estimated risk is reduced by use of one or more of several techniques to perturb the data, such as suppressing the search results entirely, intentional suppression of specific matching returned records, inclusion of patient data from a wider selection criteria (e.g., a wider age band), intentionally returning patient records that do not meet all of the selection criteria, and so forth. However, these techniques necessarily degrade the returned data, with resulting effects on any findings based upon the degraded returned data. Therefore, estimation of the risk of re-identification is important, because overestimating the risk will result in a patient dataset that has been unnecessarily degraded, but underestimating the risk will result in release of data that is overly susceptible to re-identification.

Embodiments in accordance with the present disclosure provide an improved estimation of a risk of re-identification, an improved estimation of how to reduce the risk, and an improved throughput. Improved estimation helps avoid unnecessary degradation of patient data used for medical studies, and helps avoid release of data that is susceptible to re-identification. Patient privacy is enhanced, and medical studies have access to better quality data.

Exemplary populations 110, 106, 104 and a sample 102 are described in relation to FIG. 1. The sample 102 in this case contains one person, the target. Sample 102 represents nine people 104 in the represented population 104, i.e. the target looks like eight other people in the represented population 104.

The sample 102 contains a randomly selected person from the prevalent population 106. This is the group of people who could be in the dataset. i.e., if the dataset is about cancer, then the prevalent population 106 is all people who have cancer. In this example the prevalence is ⅕, or 18 people have breast cancer and could be in the dataset. This group of 18 people will be called the prevalent population 106 to indicate the relationship to disease and that population size*prevalence=prevalent population size.

The sample 102 is a subset of the prevalent population 106, one patient in this case, and the one patient looks similar only to half of prevalent population 106. Thus, k=1, K=9, and N=18, where N is the prevalent population size.

The population 110 contains everyone, even people who do not have cancer. The sampling fraction is defined as the ratio between the sample 102 and the prevalent population 106. The represented fraction is defined as the ratio between the sample 102 and the represented population 104. From this point on, the prevalent population 106 will be referred to as the population.

In embodiments, Quasi-Identifiers (QIs) are sub-divided into categories based on the largest (i.e., most general) group of people who can know a piece of information, either public information or acquaintance information.

Public information: This information (i.e., data) is either publically available or the recipient has this data. Public data should be structured, accessible to the recipient, and cover a large portion of the population, such as 1% or greater. A good test for public knowledge is "could the recipient look up this value for a large percentage of randomly selected people." While self-disclosure and newspapers are public knowledge, they are not structured and do not cover a large part of the population.

Acquaintance information: This is information about one person (i.e., the subject) that may be known by a second person (i.e., the acquaintance) if the acquaintance is familiar with the subject, or if the acquaintance sees the subject. Acquaintance level knowledge also includes public information on celebrities and public figures that have their personal lives disclosed.

Acquaintance knowledge is not required to be structured or centralized, however it should be knowable by many acquaintances. A good test is "Would at least 50% of your acquaintances know this value?"

Figure 2:
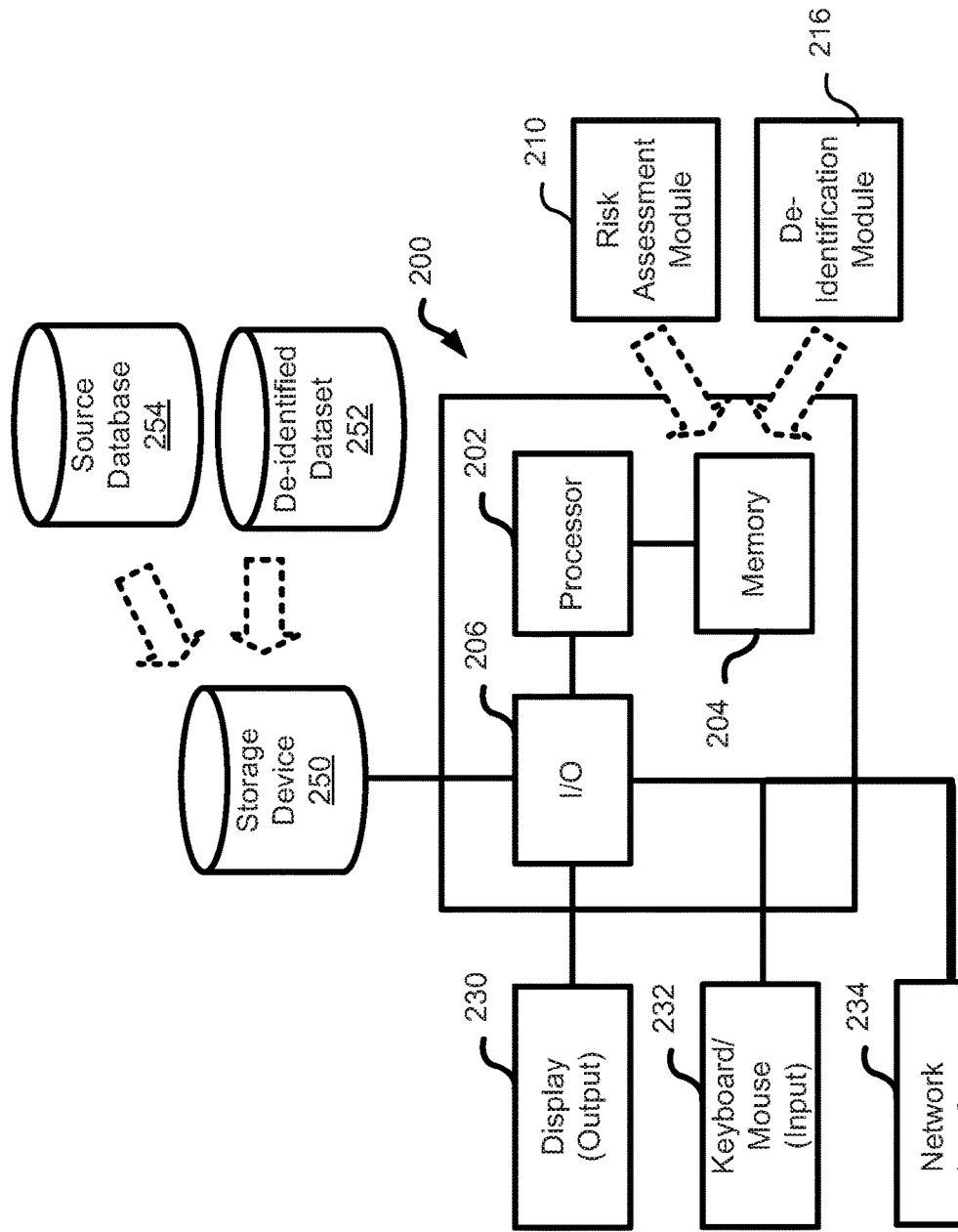
FIG. 2 shows a representation of system for determining re-identification risk of dataset in accordance with an embodiment of the present disclosure.

FIG. 2 shows a system 200 for performing risk assessment of a dataset, in accordance with an embodiment of the present disclosure. System 200 executes on a computer including a processor 202, memory 204, and input/output interface 206. Memory 204 executes instruction for providing a risk assessment module 210, which performs an assessment of re-identification risk. The risk assessment may also include a de-identification module 216 for performing further de-identification of the database or dataset based upon the assessed risk. A storage device 250, either connected directly to the system 200 or accessed through a network (not shown) stores the de-identified dataset 252 and possibly the source database 254 (from which the dataset is derived) if de-identification is being performed by the system. A display device 230 allows the user to access data and execute the risk assessment process. Input devices such as keyboard and/or mouse provide user input to the I/O module 206. The user input enables selection of desired parameters utilized in performing risk assessment, but may also be selected remotely through a web-based interface via network interface 234. The instructions for performing the risk assessment may be provided on a computer readable memory. The computer readable memory may be external or internal to the system 200 and provided by any type of memory such as read-only memory (ROM) or random access memory (RAM). The risk assessment process can determine a risk for population to sample and sample to population type attacks in order to aid in determining quasi-identifier de-identification or anonymization strategies to be applied to the dataset.

Standard de-identification techniques known in the art include generalization, suppression, and subsampling. Suppression is a targeted technique that removes individual values from a dataset in order to lower the risk to an appropriate level. The values chosen should be in line with the risk measurement approach in order to maximize the impact of each suppression event. Previous approaches for performing suppression involved a slow iterative process and did not specifically target the most problematic fields. Methods of the background art use an iterative approach to finding an appropriate suppression scheme. A candidate suppression scheme is applied, and the risk of the resulting dataset is determined. If the risk is high, a new scheme is developed which applies more suppression, whereas if the risk is excessively low a new scheme is developed which applies less suppression. The process iterates until the process converges.

Embodiments in accordance with the present disclosure reduce an amount of data manipulation required in order to achieve a low risk dataset.

Embodiments provide a framework and process for suppression and risk measurement. The framework facilitates usage of interchangeable components to configure the suppression and risk measurement process. Embodiments require only one pass over the data to achieve a low risk of re-identification. The result is a low risk dataset that includes some suppression (or a list of changes required to achieve acceptable risk) and a risk measurement of the dataset.

Embodiments in accordance with the present disclosure improve upon the background art by reducing re-identification risk to an acceptable level in one pass by use of an anonymity histogram, from a plurality of calculated anonymity values, to estimate a number of data subjects who are unique in the dataset.

The anonymity histogram may be useful to predict what suppression (e.g., fields and values) is needed in order to achieve an acceptable level of re-identification risk. Techniques to produce and to use the anonymity histogram are described in parent application Ser. No. 15/320,240, the content of which is hereby incorporated by reference in its entirety. The parent document discloses a system and method to characterize probability distributions of unperturbed data.

The anonymity histogram is a novel data structure determined using information theory, in order to measure an overall risk of re-identification. Anonymity histograms are one or two-dimensional arrays (e.g., an array or matrix), where the x-axis is population anonymity (usually an integer), and optionally a y-axis with sample anonymity. Cell counts are the number of patients with that set of anonymity values.

Embodiments in accordance with the present disclosure use novel risk prediction processes and novel risk measurement processes. Embodiments also provide usage of computer-implemented data structures that are novel in this usage space. The anonymity histogram data structure combined with risk prediction using histograms helps enable selection of a suppression amount that is predicted to lower the risk of re-identification to an acceptable level. Embodiments in accordance with the present disclosure address the following problems and include at least the following benefits.

First, previous methods of the known art required iteration and multiple passes between suppression and risk measurement, and consequently were relatively slow, due in part to iteration. In contrast, embodiments in accordance with the present disclosure are novel at least because they require only a single pass over the dataset and apply suppression in one pass, by use of a novel risk prediction methodology and using a risk measurement approach that treats the population as invariant, given a suppression threshold and an anonymity histogram. This approach gives novel choices for the selection of values to suppress, in order to increase the desired data quality. For example, a smart suppression value selector attempts to balance a desired final state of the data with data quality, by preferentially suppressing independently distributed values instead of correlated values. This preference also can be stated as a preference to perturb low-correlation values (i.e., values relatively uncorrelated with other values) over high-correlation values (i.e., values relatively correlated with at least some other values).

In particular, embodiments assume that the risk to an individual logistic source population is measured. The population, which may be estimated using the original dataset, is considered to be involatile and constant. In contrast, the background art relied on comparing individuals in the dataset against the rest of the dataset. Therefore, any time the background art would make a change to one individual, the change could have cascading re-identification problems for other people in the dataset.

Furthermore, embodiments provide a more predictable response to suppression due to treating the underlying population as being invariant. This has the effect of requiring less overall suppression and not requiring multiple iterations to find a low risk solution. Previous methods of the known art in some circumstances would see a suppression action to one record increase the risk to another record elsewhere in the dataset. For example, consider a patient with a rare diagnosis (e.g., occurring in 5 individuals) and a common diagnosis (e.g., occurring in 10,000 individuals). Suppressing the rare diagnosis in this individual lowers the risk for this record, but may raise the risk of other individuals with the rare diagnosis, which would now occur in only 4 individuals. Similarly, even if the suppression is applied to all instances of the rare event, then the risk for each individual will need to be re-evaluated based on a different subset of values, and may not result in an overall decrease in risk. In contrast, the embodiments employ a risk measurement approach that treats the underlying population as being invariant. Thus per the previous example, even though the rare diagnosis would be suppressed from a single record, the risk for all other individuals would continue to be based on this rare value being shared among a fixed percentage of the population.

By treating the underlying population as being invariant, embodiments make a reasonable assumption that the total population does not change significantly, relative to its initial size, during the time it takes to compute the de-identified dataset. So any statistics that may have been computed before producing a de-identified dataset still will be deemed to be valid after producing the de-identified dataset. Suppression does not significantly change any facts about the total population.

A third benefit is that an impact of a given suppression action upon a risk measurement can be immediately, accurately and precisely quantified. This provides insight, which embodiments can leverage to improve the risk reduction in future suppression actions. In contrast, previous methods of the known art were not based on the actual risk profile, but rather used a very rough heuristics that were not accurate or precise.

A fourth benefit is that embodiments facilitate support of various data quality metrics, and facilitate maintenance of a threshold level of data quality in accordance with a desired risk reduction approach. Examples of data quality metrics may include one or more of: (1) Correlations among values, such that embodiments prefer to suppress independently distributed values in order to maintain correlations among other values; (2) Percentage of cells suppressed per column, maintained via a value selector; (3) Percentage of patients with suppression, which is improved by shotgun suppression; (4) Balancing the number of columns or values suppressed in patient profiles instead of just least common, maintained via a value selector; (5) Prioritization of columns or fields in the patient profile to suppress, based upon client preference or aversion. In contrast, previous approaches of the known art used a one-size-fits-all solution, which gave little to no control over the resulting dataset. Previous approaches lacked insight into what efficiently lowers risk, leading to ineffective suppression actions with decreased data quality, without a corresponding increase in privacy.

A fifth benefit is that embodiments reduce a risk of imputation attacks (i.e., reconstituting the removed values based on other values in the dataset), compared to previous approaches of the known art. Imputing a value for a field in a data record also may be referred to as inferring a value for the field in the data record. This form of imputation is based on knowledge of the suppression process. If the process is known to suppress the rarest diseases in a patient, then when an adversary sees a missing disease condition, an adversary can assume the missing disease condition must be at least as rare as the rarest disease condition that is not suppressed for this patient. For example, if embodiments always show the rarest value in a patient's record, and embodiments indicate that the patient had been diagnosed with a rare disease or condition (e.g., botulism), but if there is another value that has been suppressed, then the other value that was suppressed had to be even more uncommon than the first rare condition So, the imputed value would not be indicative of, e.g., the flu or chickenpox.

Because the selection method of a value/cell/field to suppress is separate from a calculation of statistics, embodiments may accept user input (e.g., through settings, preferences or the like) as to how values should be suppressed. For example, for a study of rare events like incidences of botulism, embodiments may tune the suppression process, for example, by not suppressing data values that are associated with the rare event, or are a result of the rare event. On the other hand, medical studies often look for large trends, but rare events provide so few data points that they are not analytically valuable. So in that case, when not studying the rare events themselves, the rare events would be the events to suppress.

In embodiments, things that occur very rarely have essentially no analytic value if they are not specifically being studied. Even if they are not specifically being studied, often there are not enough data points involving the rare events to calculate statistically meaningful correlations. Therefore, such rare events can be suppressed unless they are specifically being studied. Correlations are referred to in their ordinary statistical sense as a numeric measure of how one parameter varies with another parameter. Correlations may take on numeric values within the range [−1.0, 1.0], inclusive.

When suppression is applied using a uniform random variable, the underlying distribution of each variable should still be consistent (aside from some noise, which can average out over large amounts of data), but the strength of correlations may be impacted. In further embodiments of smart suppression, it is preferred to select values for a patient that are statistically independently from other values related to the patient. To permit detection of correlations between data items (i.e., pointwise mutual information), embodiments avoid suppressing data items that may have correlated information, for two reasons. First, correlated information is analytically interesting, e.g., by highlighting symptoms, side effects, etc. For example, researchers may be interested in whether condition "X" is correlated with condition "Y".

Second, suppose condition X (e.g., pregnancy or breast cancer) is highly correlated with condition Y (e.g., female gender). Then even if condition Y is suppressed, its value may be inferred with high assurance from knowledge of condition X. Therefore, the two conditions share information. So suppressing a field that is highly correlated with another field may not be effective unless the correlated fields also can be suppressed.

At a high level of abstraction, a threshold selector may be used to select which patient's profile within a dataset will be perturbed. A value selector may be used to choose which values within that patient's profile will be perturbed. For example, a value selector may be designed that is responsive to a query for the study of botulism. The value would be configured to avoid picking values related to botulism for suppression. Furthermore, the value selector also may be designed to avoid picking anything that is correlated with botulism. In contrast, such suppression would allow the suppression of common medical history values such as a cold or the flu, as long as the value is not botulism or a condition highly correlated with botulism.

Figure 3:
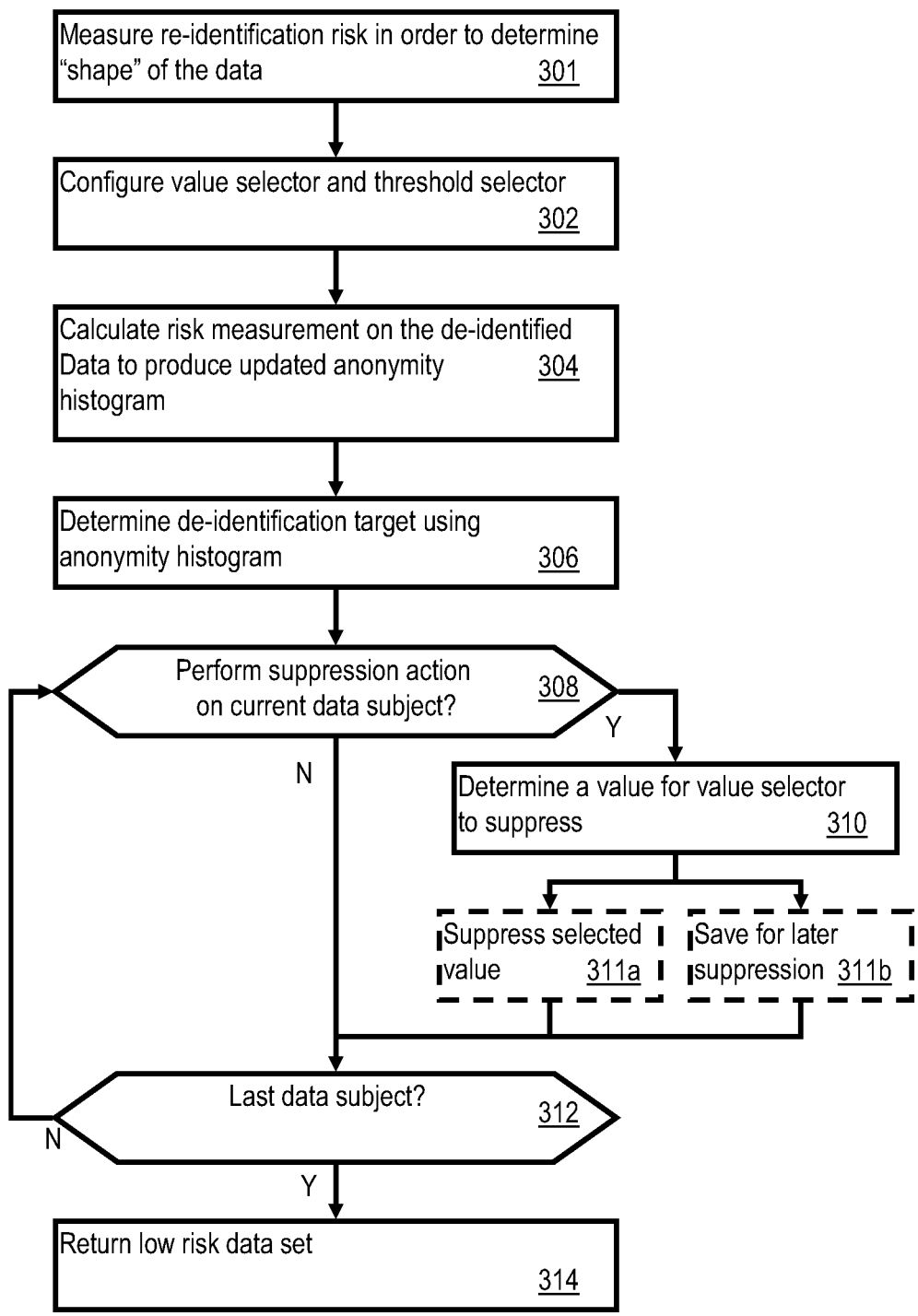
FIG. 3 shows the process for lowering the risk of re-identification by applying suppression.

FIG. 3 illustrates a process 300 in accordance with an embodiment of the present disclosure. Process 300 may be used to choose a value selector and choose a threshold selector.

Process 300 begins at step 301, at which a first pass of the data is performed, to measure re-identification risk of the dataset, in order to determine the anonymity histogram of the data. The anonymity histogram is used by a threshold selector to determine how to lower the re-identification risk.

Since anonymity is normally a real value (i.e. continuous or decimal), if anonymity values are converted into an integer value, an anonymity profile of dataset can be concisely expressed. In part, this is because anonymity is in a logarithmic scale, expressing magnitudes of difference. However, operations like round, round-up (i.e., ceiling), round-down (i.e., floor), will change the average risk profile of the anonymity histogram. An anonymity histogram may be used to model population anonymity and maintain an average risk profile of a sample to population re-identification.

The anonymity histogram makes use of re-ID bits, which is how much information can be obtained about a person before that person is expected to be unique in the dataset. The anonymity histogram also makes use of given bits, which is a measure of how much information is present about that person in the dataset. Thus, the anonymity of a person is the difference between these two quantities, i.e., the re-ID bits minus the given bits.

Given the anonymity so described, the process then may bucket the data to mask insignificant variations (i.e., integer anonymity values). The result, when plotted, is an anonymity histogram having an X-axis of integer anonymity values, and a Y-axis of a number of people in each of those buckets. The anonymity histogram may reveal buckets of people with positive anonymity. So relatively minor perturbations to those persons may cause those persons to resemble many other persons in the dataset. People who have a huge amount of information associated with them ordinarily will then have a negative anonymity value. For such persons, embodiments may make significant perturbations before the risk measurement of re-identification would be significantly impacted.

The anonymity histograms may be available in at least two formats. One format is an array in which each cell of the array indicates an integer anonymity (e.g., one, zero, negative one, negative two, negative three), and the value in the cell would be a number of patients. Another format is a two-dimensional format, with the two axes having different degrees of anonymity, i.e., sample and population anonymity.

Given an initial risk measurement, anonymity histogram and threshold selector, embodiments may process each patient in the dataset. With each patient record, the threshold selector determines whether or not data for that patient should be perturbed. If the data is not to be perturbed, then the process moves on to a next patient. However, if the patient record is to be perturbed, then the process considers a value selector as described below.

The threshold selector determines the method of getting a low risk solution, and tries to optimize certain types of data quality. The threshold selectors use the anonymity histogram and use the prediction framework to find a solution that provides a lower risk dataset.

Threshold selectors may be one of "shift", "shotgun", "truncation", "amortized truncation", or "amortized shift/shotgun", as described below.

A shift threshold selector may be used to obtain low risk by applying a small amount of suppression to all data subjects. The shift threshold selector usually results in lower cell level suppression compared to truncation.

A shotgun threshold selector may be used to obtain low risk by applying relatively more suppression than used for the shift threshold selector on a subset of data subjects. The size of the subset of data subjects, as indicated by an associated sampling fraction, is user configurable. The shotgun threshold selector results in fewer patients having suppression.

A truncation threshold selector may be used to apply suppression until all data subjects reach a predetermined minimum threshold of anonymity. Anonymity is known as a measure of how anonymous are the data subjects. For example, anonymity may be quantified by how many members of a dataset (or what percentage of the dataset) share certain characteristics. By using the truncation threshold selector, some data subjects may require a relatively large amount of suppression, whereas other data subjects who already meet the threshold of anonymity may require no suppression or no further suppression. The truncation threshold selector is effective to provide a guaranteed level of anonymity.

An amortized truncation threshold selector may be used to apply truncation suppression. However, using the amortized truncation threshold selector would attempt to meet an average risk threshold instead of all data subjects meeting a minimum anonymity. In other words, some individual data subjects may not meet a minimum anonymity, so long as the overall dataset meets the minimum anonymity threshold. Use of an amortized truncation threshold selector attempts to strike a balance between over-shoot and under-shoot of the average risk threshold.

An amortized shift/shotgun threshold selector is a variant of both a shift threshold selector and a shotgun threshold selector. The amortized shift/shotgun threshold selector balances over-shoot and under-shoot in order to achieve a target average risk with less suppression than shift or shotgun would do individually. These threshold selectors minimize the number of cells and/or patients with suppression, which achieves a lower risk dataset with relatively minimal overshoot of the average risk threshold.

Next, value selectors are used to determine which value(s) to suppress next. Value selectors allow for a focus on data quality of a specific type, or a balance of suppression across columns or fields in the patient profile. Value selectors are not necessarily required to select optimal values, or even a value that lowers risk (e.g., risk may stay the same but will not increase). However, without smart value selectors, it is possible that the improved value might result in over-shoot, i.e., lowering the risk more than is necessary. On the other hand, under-shoot is a technique that a threshold selector may use to apply less suppression to one data subject because the previously examined data subject had suppression over-shoot (i.e., the risk was lowered more than was strictly required).

Value selectors may be one of "lottery", "ordered", "maximal", "outlier selector", and "smart", as described below. As an example to understand the difference between the value selectors, consider in the scenarios below a patient with the following QI values A, B, C, D with 8, 4, 2, 1 bit of information respectively. Now also consider below that the threshold selector (e.g., shift) has determined that each patient requires a 2 bit increase in anonymity.

A lottery value selector may be used when a suppression preference weight is assigned to each value field of a data subject. The suppression preference weight may be analogized to a number of tickets this value could buy for a lottery. For example, for a given data subject, each value may "buy" all of the tickets allocated to that value (i.e., figure out how many tickets are distributed to different values). Selecting a winning lottery ticket is analogous to a suppression of a data subject value that corresponds to the winning lottery ticket.

Considering this example using a lottery value selector, we assign A, B, C, D weights: w(A), w(B), w(C), w(D). Thus the probability of value A being randomly selected is w(A)/(w(A)+w(B)+w(C)+w(D)). A value to suppress will be chosen randomly based on these probabilities. If D is chosen, it will not satisfy the threshold selector and thus a second value will also be suppressed to meet the requirement. If A or B are chosen then we have over-shoot of the threshold by 7 or 3 bits, respectively.

An ordered value selector may be used when a user specifies an order (i.e., sequence) for which values should be considered for suppression. Using this selector involves selecting a random value from the values with the highest priority (highest order). If two values are tied for highest priority, one is randomly selected for suppression.

Consider our example using a ordered value selector, we must assign A, B, C, D priorities: p(A), p(B), p(C), p(D). For the purpose of the example, let us consider the following priorities: p(D)=4, p(A)=p(B)=3, p(C)=1. Larger numbers have higher priority. First D will be selected for suppression, because it has the highest priority. However this will not satisfy the threshold selector, so another value must be suppressed. Either A or B will be randomly selected for suppression, because they are tied for the next highest priority. This results in over-shoot since threshold selector only required 2 bits of suppression and we have suppressed 9 or 5 bits.

A maximal value selector may be used when picking a value that provides the most information in an information theory sense. The maximal approach is based upon Information Theory and using a risk measurement approach. Consider our example using a maximal value selector. A will be selected for suppression because it is the most information value. This results in over-shoot since threshold selector required only 2 bits of suppression and we have suppressed 8 bits. However, unlike previous examples, fewer cells have been suppressed.

An outlier value selector may be used when setting a value "k", indicating a minimum acceptable frequency of occurrence for all or an associated value ("k" refers to the number of patients who have the value). Using this selector involves choosing a value for k that occurs with the lowest frequency of occurrence for this patient (i.e., occurring less than k times). The outlier value selector may not necessarily lead to a low risk solution on its own.

Consider the earlier example using an outlier value selector. Outlier values ordinarily will have high information values because they occur rarely and the rate of occurrence defines the information value. Suppose the data is from a population of 256 people, thus A=8 bits of information would occur in 1 person, B=4 bits of information would occur in 16 people, C would occur in 64, and D in 128 people. Let us assume the user has set k=8. Outlier suppression will suppress A because it occurs once in the population. All other values occur more than 8 times in the population, and will not be suppressed.

A smart value selector may be used when a suppression process is programmed to return a low risk result, while minimally impacting data quality. The threshold selector should pass a target value to the smart value selector. For better results, often there are tradeoff between suppressing values in L1 (primary table) and L2 (claims table). The user should provide a value or function indicating how strict the process should be (e.g., an epsilon tolerance function). The user should also set the acceptable target suppression (e.g., as a percentage suppression for each column or type).

An epsilon tolerance function will take an acceptable state ("as") (i.e., the acceptable amount of suppression in the final dataset), current state ("cs") (i.e., how much suppression we have currently applied), a tolerance ("t"), and a value ("v") being consider for suppression: £(as, cs, t, v). The epilson tolerance function returns the error (or cost) of the deviation from as if we suppress v. The tolerance t, a value between 0 and 1, indicates whether we should prefer minimization of data quality loss (e.g., total cells suppressed, overshoot, or suppress correlated values) or adhering of as. Embodiments now solve a local minimization problem: each time the smart value selector is called, embodiments will choose the value v, from the set of values that may be suppressed, which minimizes result of the epsilon tolerance function.

The epsilon tolerance function indicates how far a returned dataset can deviate from a target acceptable suppression in favor, of maintaining overall higher data quality. Furthermore, selection of variables to be suppressed may take into account mutual information, i.e., correlations. Variables without mutual information are independent and suppression of them should not affect analysis correlations, which in turn should give better data quality, compared to suppression of correlated variables. An epsilon tolerance function should increase the cost (or error) of suppressing a value with high mutual information.

The value selector determines what value from the patient profile should be suppressed. After performing the suppression of the selected value, the re-identification risk measurement for that individual patient is updated, and the process goes back to considering the threshold selector. The threshold selector indicates if more suppression is needed (i.e., did the suppression action meet the criteria required by the threshold selector). If the answer to that question is positive (i.e., yes, enough suppression has been applied), then the threshold selector portion of the process is finished with that patient. If the answer to that question is negative (i.e., more suppression is required), then the value selector will choose an additional value to suppress in the data record for the patient. This process will loop and continue for this patient until the threshold selector is satisfied or there is no data left. Once the process is finished with one patient, the process will return the patient to the pool and move on to the next patient. In this manner, the process may take one pass through the entire dataset. Once the one pass through the dataset is completed, the result is a dataset with a low risk of re-identification.

Next, process 300 moves to step 302, at which a value selector and a threshold selector are configured. The act of configuring may be done by a user (e.g., a data analyst) or selected by a computer running under programmatic control.

A threshold selector is selected, which determines a scheme to obtain low risk. For example, suppose a high risk dataset is presented to an embodiment in order to reduce the re-identification risk. Embodiments may provide a module interface, e.g., an interface to a module to calculate re-identification risk. Such a module may be designed to accept as input an anonymity histogram that represents a data distribution within the dataset. Then, throughout the measurement process, embodiments may use the module to verify whether a proposed suppression would be effective to reduce the risk of re-identification.

The module may be designed to accept limited user configuration control, e.g., whether the module should modify records for all patients minimally, or should the module modify a subset of patients by a larger amount. The modification may be a suppression, but in other embodiments the modification may be a local recoding of a value. A local recoding may be used in place of putting a NULL or deleting a value, such that embodiments instead would write a fictional value that is a resynthesized generalization of the original. The fictional value would be a less accurate value, but still close in value to the original value. A broad but small modification may be referred to herein as a shift approach. A larger but more targeted modification may be referred to herein as a shotgun approach. The shift approach is designed to affect more individuals, but do less to their data records. The shotgun approach affects fewer individuals, but does more to each of their data records. Either approach may be preferred, depending on the composition of a specific dataset.

Embodiments also may take into account an absolute level of re-identification risk already existing in a dataset, prior to application of suppression or other modification. Such an approach may provide improved data quality, in which data quality is quantified by how little a dataset was modified or needs to be modified. For example, if two datasets have equal risk of re-identification, the dataset that had been less modified is deemed to be of higher quality.

Next, process 300 transitions to step 304, at which a calculation of risk measurement is performed on the de-identified data, in order to return an updated anonymity histogram. Step 304 may use a risk measurement sub-process that uses prior population distributions. A prior population distribution is a probability distribution of a variable for the population, and is part of risk measurement process. The distribution describes, for a specific variable, the percentage of the population with this value, condition, or property. This measurement technique of using prior population distributions means that suppression does not change the prior population distributions, and risk measurement will not increase either globally (i.e., over the whole dataset) or locally (i.e., for a single data subject).

Next, process 300 transitions to step 306, at which a threshold selector uses the anonymity histogram to determine a de-identification target that provides a risk below a predetermined threshold level of risk. The de-identification target is used to try to achieve a sufficiently low-risk dataset. Selectors express the target differently. For example, shift selector may express that each patient must have an increase in anonymity of X bits. Shotgun selector may express that Y percent of patient require an increase in anonymity of X bits.

Next, process 300 transitions to decision step 308 at which, for a current data subject, determine per the threshold selector whether a suppression action should be performed on the current data subject. If the result of step 308 is positive, then proceed to step 310. If the result if step 308 is negative, then proceed to step 312.

At step 310 of process 300, the value selector determines a value to suppress in the current data subject. At the conclusion of step 310, control of process 300 transitions to either step 311a or step 311b, depending upon whether process 300 has been configured to suppress data right away or to create a log file for later suppression, respectively.

At step 311a, the value selected by the value selector is suppressed. In a different embodiment, rather than applying the suppression immediately, step 311b is performed at which an instruction is written to storage (e.g., to a log file) that this value should be suppressed. In this case, suppression may be applied at a later time. Upon completion of step 311a or 311b, control of process 300 transitions to step 312.

At decision step 312, a test is performed whether this was the last data subject. If the outcome of decision step 312 is positive, then control of process 300 transitions back to step 308. If the outcome of decision step 312 is negative, then control of process 300 transitions to step 314.

At step 314, the low risk dataset is returned to the user (e.g., a data analyst).

Figure 4:
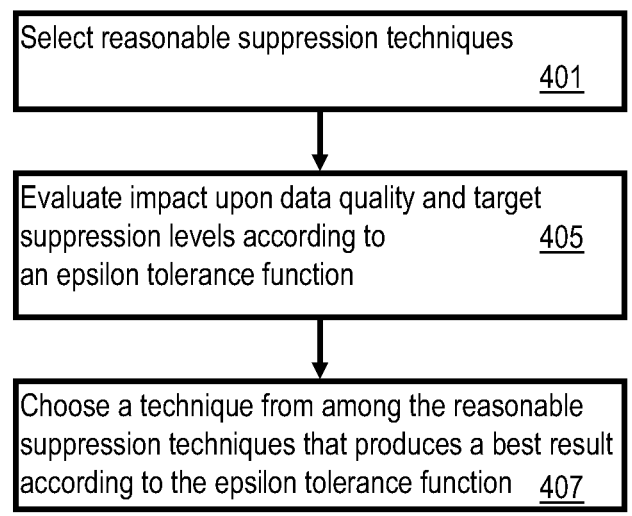
FIG. 4 illustrates a process to select a smart suppression technique and value selector.

FIG. 4 illustrates a process 400 of smart suppression, which may be usable as step 310 of process 300. Process 400 begins at step 401, at which all possible suppression techniques are considered in order to reach a target anonymity. At a high level, some of these techniques might include suppressing a demographic value, suppressing longitudinal values, and suppressing a mix of demographic and longitudinal values, suppressing independently distributed values, and/or suppressing outlier values. Techniques may include choosing a value or combination of values that minimizes over-shoot.

Next, process 400 progresses to step 405, to evaluate impact upon data quality and target suppression levels according to an epsilon tolerance function.

Next, process 400 progresses to step 407, to choose a technique from among the reasonable suppression techniques of step 401 that produces a best result according to the epsilon tolerance function. The chosen technique will locally minimize cost returned from the epilson tolerance function.

Smart suppression can consider outlier suppression (or outlier value selector) as one possible technique to lower risk.

Each element in the embodiments of the present disclosure may be implemented as hardware, software/program, or any combination thereof. Software codes, either in its entirety or a part thereof, may be stored in a computer readable medium or memory (e.g., as a ROM, for example a non-volatile memory such as flash memory, CD ROM, DVD ROM, Blu-ray™, a semiconductor ROM, USB, or a magnetic recording medium, for example a hard disk). The program may be in the form of source code, object code, a code intermediate source and object code such as partially compiled form, or in any other form.

It would be appreciated by one of ordinary skill in the art that the system and components shown in FIG. 2 may include components not shown in the drawings. For simplicity and clarity of the illustration, elements in the figures are not necessarily to scale, are only schematic and are non-limiting of the elements structures. It will be apparent to persons skilled in the art that a number of variations and modifications can be made without departing from the scope of the invention as defined in the claims.

Embodiments of the present disclosure include a system having one or more processing units coupled to one or more memories. The one or more memories may be configured to store software that, when executed by the one or more processing unit, allows practice of the embodiments described herein, at least by use of processes described herein, including at least in FIGS. 3-4, and related text.

The disclosed methods may be readily implemented in software, such as by using object or object-oriented software development environments that provide portable source code that can be used on a variety of computer or workstation platforms. Alternatively, the disclosed system may be implemented partially or fully in hardware, such as by using standard logic circuits or VLSI design. Whether software or hardware may be used to implement the systems in accordance with various embodiments of the present disclosure may be dependent on various considerations, such as the speed or efficiency requirements of the system, the particular function, and the particular software or hardware systems being utilized.

While the foregoing is directed to embodiments of the present disclosure, other and further embodiments of the present disclosure may be devised without departing from the basic scope thereof. It is understood that various embodiments described herein may be utilized in combination with any other embodiment described, without departing from the scope contained herein. Further, the foregoing description is not intended to be exhaustive or to limit the disclosure to the precise form disclosed. Modifications and variations are possible in light of the above teachings or may be acquired from practice of the disclosure. Certain exemplary embodiments may be identified by use of an open-ended list that includes wording to indicate that the list items are representative of the embodiments and that the list is not intended to represent a closed list exclusive of further embodiments. Such wording may include "e.g.," "etc.," "such as," "for example," "and so forth," "and the like," etc., and other wording as will be apparent from the surrounding context.

No element, act, or instruction used in the description of the present application should be construed as critical or essential to the disclosure unless explicitly described as such. Also, as used herein, the article "a" is intended to include one or more items. Where only one item is intended, the term "one" or similar language is used. Further, the terms "any of" followed by a listing of a plurality of items and/or a plurality of categories of items, as used herein, are intended to include "any of," "any combination of," "any multiple of," and/or "any combination of multiples of" the items and/or the categories of items, individually or in conjunction with other items and/or other categories of items.

Moreover, the claims should not be read as limited to the described order or elements unless stated to that effect. In addition, use of the term "means" in any claim is intended to invoke 35 U.S.C. § 112(f), and any claim without the word "means" is not so intended.

What is claimed is:

1. A method to produce an anonymized cohort that includes members having less than a predetermined risk of re-identification, comprising:
    on a processor coupled to a network communication channel and a data source:
    receiving a request for an anonymized cohort, identifying one or more traits to include in the members of the anonymized cohort;
    forming a dataset from a plurality of records from the data source having at least one of the traits, each of the plurality records describing a patient profile;
    calculating an anonymity histogram of the dataset, wherein the anonymity histogram comprises a calculation based upon
        re-identification bits to indicate how much information is obtained about a patient before that patient is unique in the dataset, and
        given bits to indicate how much information is present about the patient in the dataset;
    for each of the plurality of records within the dataset:
        determining, using a threshold selector, whether the patient profile should be perturbed;
        selecting preferring to perturb low-correlation values over high-correlation values; and
        suppressing the selected value.

2. The method of claim 1, further comprising a step of logging the suppressed value.

3. The method of claim 1, wherein the dataset comprises an invariant population.

4. The method of claim 1, wherein the threshold selector comprises a shift threshold selector, and further comprising a step of using the shift threshold selector to obtain an anonymized dataset by applying a small amount of suppression to all patient profiles.

5. The method of claim 1, wherein the threshold selector comprises a shotgun threshold selector, and further comprising a step of using the shotgun threshold selector to obtain an anonymized dataset by applying, on a subset of patient profiles, relatively more suppression than provided by a shift threshold selector.

6. The method of claim 1, wherein the threshold selector comprises a truncation threshold selector, and further comprising a step of using the truncation threshold threshold selector to obtain an anonymized dataset by applying suppression until all patient profiles reach a predetermined minimum threshold of anonymity.

7. The method of claim 1, wherein the threshold selector comprises an amortized truncation threshold selector, and further comprising a step of using the amortized truncation threshold selector to obtain an anonymized dataset by attempting to meet an average risk threshold instead of all patient profiles meeting a minimum anonymity.

8. The method of claim 1, wherein the threshold selector comprises an amortized shift/shotgun threshold selector to obtain an anonymized dataset by balancing over-shoot and under-shoot in order, and further comprising a step of using the amortized shift/shotgun threshold selector to achieve a target average risk with less suppression than a shift threshold selector and a shotgun threshold selector would do individually.

9. The method of claim 1, wherein the value selector comprises a suppression preference weight assigned to each value field of the patient profile.

10. The method of claim 1, wherein the value selector comprises an ordered value selector to specify an order for which values should be considered for suppression.

11. The method of claim 1, wherein the value selector comprises a maximal value selector to use information theory sense-based information, and further comprising a step of using the maximal value selector when selecting the value from the patient profile that provides the most information.

12. The method of claim 1, wherein the value selector comprises an outlier value selector, and further comprising a step of using the maximal value selector to specify a minimum acceptable frequency of occurrence for an associated value in the patient profile.

13. The method of claim 1, wherein the value selector comprises a smart value selector, and further comprising a step of using the maximal value selector to specify value determined by the threshold selector.

14. The method of claim 1, wherein the step of using the value selector further comprises steps of:
   using an epsilon tolerance function to determine an acceptable state as a function of a current state and a value being considered for suppression, and
   returning a cost of a deviation from the acceptable state as the value being considered for suppression is suppressed.

15. A system to produce an anonymized cohort that includes members having less than a predetermined risk of re-identification, comprising:
   a processor coupled to a network and to a data source, the processor is configured to:
   receiving a data query via a user-facing communication channel to receive a request for an anonymized cohort, identifying one or more traits to include in the members of the anonymized cohort;
   forming form a dataset from a plurality of records from the data source having at least one of the traits, each of the plurality records describing a patient profile;
   calculate an anonymity histogram of the dataset;
   for each of the plurality of records within the dataset:
      determine, using a threshold selector, whether the patient profile should be perturbed, the threshold selector comprises an amortized shift/shotgun threshold selector to obtain an anonymized dataset by balancing over-shoot and under-shoot in order, and further comprising a step of using the amortized shift/shotgun threshold selector to achieve a target average risk with less suppression than a shift threshold selector and a shotgun threshold selector would do individually;
      select, using a value selector, a value within the patient profile that should be perturbed; and
   suppress the selected value.

16. A method to produce an anonymized cohort that includes members having less than a predetermined risk of re-identification, comprising:
   on a processor coupled to a network communication channel and a data source:
   receiving a request for an anonymized cohort, identifying one or more traits to include in the members of the anonymized cohort;
   forming a dataset from a plurality of records from the data source having at least one of the traits, each of the plurality records describing a patient profile;
   calculating an anonymity histogram of the dataset;
   for each of the plurality of records within the dataset:
      determining, using a threshold selector, whether the patient profile should be perturbed, the threshold selector including an amortized shift/shotgun threshold selector, wherein the amortized shift/shotgun threshold selector is used to obtain an anonymized dataset by balancing over-shoot and under-shoot in order to achieve a target average risk with less suppression than a shift threshold selector and a shotgun threshold selector would do individually;
      selecting, using a value selector, a value within the patient profile that should be perturbed; and
   suppressing the selected value.

* * * * *

UNITED STATES PATENT AND TRADEMARK OFFICE
CERTIFICATE OF CORRECTION

PATENT NO. : 10,423,803 B2
APPLICATION NO. : 15/389559
DATED : September 24, 2019
INVENTOR(S) : Scaiano et al.

Page 1 of 1

It is certified that error appears in the above-identified patent and that said Letters Patent is hereby corrected as shown below:

On the Title Page

Item (63), Column 1, under "Related U.S. Application Data", after "application No. 15/320,240", and before "filed" insert --Dec. 19, 2016--.

In the Specification

In Column 14, Line 50, replace "£" with "ε".

Signed and Sealed this
Third Day of December, 2019

Andrei Iancu
*Director of the United States Patent and Trademark Office*